United States Patent [19]

Strasilla et al.

[11] Patent Number: 4,460,569

[45] Date of Patent: Jul. 17, 1984

[54] QUATERNARY, COPOLYMERIC, HIGH MOLECULAR WEIGHT AMMONIUM SALTS BASED ON ACRYLIC COMPOUNDS AND THEIR USE IN COSMETICS

[75] Inventors: Dieter Strasilla, Weil am Rhein, Fed. Rep. of Germany; Hubert Meindl, Riehen, Switzerland; Laszlo Moldovanyi, Basel, Switzerland; Charles Fearnley, Riehen, Switzerland

[73] Assignee: Ciba-Geigy Corporation, Ardsley, N.Y.

[21] Appl. No.: 425,599

[22] Filed: Sep. 28, 1982

Related U.S. Application Data

[62] Division of Ser. No. 286,920, Jul. 27, 1981, Pat. No. 4,419,344.

[30] Foreign Application Priority Data

Aug. 1, 1980 [CH] Switzerland .......................... 5876/80

[51] Int. Cl.$^3$ ............................ A61K 7/06; A61K 7/11
[52] U.S. Cl. ...................................... 424/70; 252/545; 260/456 A; 526/216; 526/217; 526/220; 526/287; 526/297; 526/307; 526/307.2; 526/317; 526/320; 526/328.5
[58] Field of Search ............... 526/287, 307, 220, 216, 526/217, 297, 317, 320, 328.5, 307.2; 260/29.6 WQ, 29.6 HN, 456 A; 424/70; 252/545

[56] References Cited

U.S. PATENT DOCUMENTS 3,759,982 9/1973 Samour ........................ 260/459 R

*Primary Examiner*—Richard A. Schwartz
*Attorney, Agent, or Firm*—Edward McC. Roberts

[57] ABSTRACT

Novel copolymeric ammonium salts which are soluble or form microemulsions in aqueous surfactant systems and which can be obtained by water-in-oil emulsion polymerization or solution polymerization of a quaternary ammonium salt of the acrylic acid series and at least one other acrylic comonomer and reaction with an anionic optionally zwitterionic surfactant, ion exchange taking place, and has a molecular weight distribution of $10^4$ to $10^9$, the molecular weight of at least 5 percent by weight of the copolymer being $10^7$ to $10^9$, can be used as cosmetics, in particular as hair cosmetics, hair treated according to the invention having excellent ease of dry combing and, in particular, ease of wet combing.

14 Claims, No Drawings

QUATERNARY, COPOLYMERIC, HIGH MOLECULAR WEIGHT AMMONIUM SALTS BASED ON ACRYLIC COMPOUNDS AND THEIR USE IN COSMETICS

This is a division of application Ser. No. 286,920 filed on July 27, 1981 now U.S. Pat. No. 4,419,344.

The present invention relates to copolymeric, quaternary ammonium salts which are soluble or give microemulsions in aqueous surfactant systems, and which have a molecular weight distribution of $10^4$ to $10^9$, the molecular weight of at least 5 percent by weight of the copolymer being $10^7$ to $10^9$, and contain, in any order, recurring structural elements of the formulae

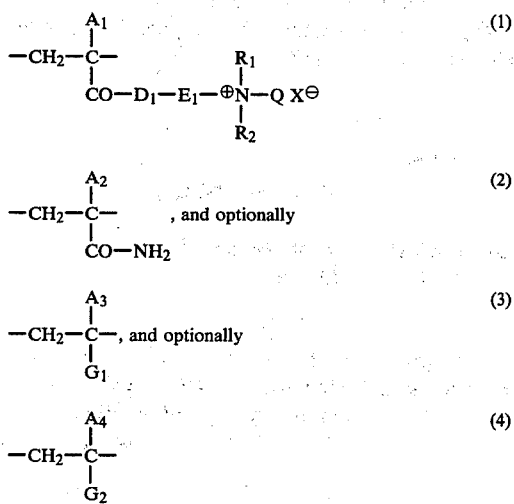

in which $A_1$, $A_2$, $A_3$ and $A_4$ are each hydrogen or methyl, $G_1$ and $G_2$ differ from one another and are each —CN, —COOH or

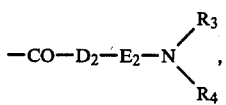

$D_1$ and $D_2$ are each oxygen or —NH—, $E_1$ and $E_2$ are each alkylene having 1 to 4 carbon atoms and which is unsubstituted or substituted by hydroxyl, $R_1$, $R_2$, $R_3$ and $R_4$ are each methyl or ethyl, Q is alkyl or hydroxyalkyl having 1 to 4 carbon atoms or benzyl and $X^\ominus$ is the radical of at least one anionic surfactant, which may be zwitterionic.

The invention also relates to the preparation process for the abovementioned copolymeric ammonium salts, their use in cosmetics, the cosmetics (hair cosmetics) which contain the ammonium salts according to the invention and methods of applying these cosmetics, in particular methods of treating hair, and hair treated by these methods, for example hair in the form of wigs.

The ammonium salts according to the invention are distinguished by the fact that they can be obtained by water-in-oil emulsion polymerisation or solution polymerisation of a quaternary ammonium salt of the acrylic acid series and at least one other acrylic comonomer, isolation of the copolymer and reaction thereof with an anionic surfactant, which may be zwitterionic, ion exchange taking place.

The water-in-oil emulsion polymerisation, which is also called inverse emulsion polymerisation, or solution polymerisation, achieves the high molecular weight range of $10^7$ to $10^9$ for the copolymers according to the invention; within the wide molecular weight distribution of $10^4$ to $10^9$, preferably 5 to 60 and in particular 20 to 50 percent by weight of the copolymers are within this high molecular weight range.

Most preferably, 30 to 45 percent by weight of the copolymers are within a molecular weight range of $10^7$ to $10^9$ and less than 15 percent by weight are in a molecular weight range smaller than $10^5$.

As well as providing the molecular weight distribution, the content of structural elements of the formula (1) in the copolymers, which is also called the quaternary content, is another essential characteristic of the ammonium salts according to the invention, these salts containing on average about 5 to 80, preferably 6 to 40 and in particular 10 to 30, mol % of structural elements of the formula (1), on average about 10 to 95, preferably 50 to 90, mol % of structural elements of the formula (2) and about 0 to 10 mol % of structural elements of the formula (3) and, optionally, (4), i.e. (3) and/or (4). Preferably, the copolymers contain no structural elements of the formulae (3) and (4). However, in cases where such structural elements are present, the copolymers contain about 1 to 8 mol % of structural elements of the formulae (3) and/or (4), and in particular in each case 1 to 4 mol % of the formulae (3) and (4).

In the formula (1), $A_1$ is preferably methyl, $D_1$ is preferably oxygen, $E_1$ is preferably unsubstituted n-propyl or, in particular, unsubstituted ethylene, $R_1$ and $R_2$ are preferably methyl and Q is preferably unsubstituted n-propyl, but preferably ethyl or, in particular, methyl. $A_2$ in formula (2) is preferably hydrogen. In formula (3), in cases where structural elements of the formula (3) are present by themselves, i.e. if no structural elements of the formula (4) are present, $A_3$ is preferably methyl and $G_1$ is preferably

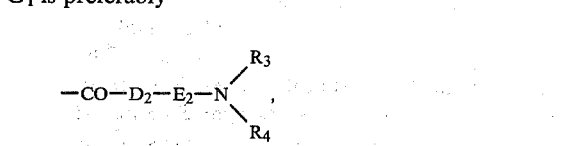

in which $D_2$, $E_2$, $R_3$ and $R_4$ are the radicals defined above as preferred for $D_1$, $E_1$, $R_1$ and $R_2$. In cases where structural elements of the formula (4) are present in addition to the structural elements of the formula (3), $A_4$ in formula (4) is preferably hydrogen and $G_2$ is preferably —CN or, in particular, —COOH.

Anionic, but not zwitterionic surfactant radicals $X^\ominus$ in formula (1) are preferably radicals of surface-active sarcosinates, sulfates, for example alkyl-sulfates, alkyl ether-sulfates, alkylamide-sulfates, alkylamide ether-sulfates, alkylaryl polyether-sulfates or monoglyceride-sulfates, sulfonates, for example alkylsulfonates, alkylamide-sulfonates, alkylarylsulfonates or α-olefinsulfonates, or sulfosuccinic acid derivatives, for example alkylsulfosuccinates, alkyl ether-sulfosuccinates, alkylamide-sulfosuccinates, alkylamide polyether-sulfosuccinates or alkyl sulfosuccinamides, and also radicals of fluorinated surfactants or phosphate surfactants, for example alkyl phosphates or alkyl ether-phosphates.

$X^\ominus$ is, for example, a sarcosinate radical of the formula

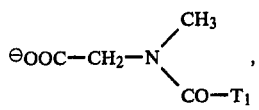 (5)

in which T₁ is alkyl or alkenyl having 7 to 21, preferably 11 to 17, carbon atoms.

The radicals T₁CO— are derived from the corresponding saturated or unsaturated fatty acids having 8 to 22, preferably 12 to 18, carbon atoms. Examples of the corresponding fatty acids are caprylic, capric, arachic and behenic acid, and in particular lauric, myristic, palmitic and stearic acid, or myristoleic, palmitoleic, elaeostearic and clupanodonic acid, and in particular oleic, elaidic, erucic, linoleic and linolenic acid. Alkyl and alkenyl radicals T₁ which are derived from industrial mixtures of the saturated and/or unsaturated fatty acids mentioned are particularly preferred. Specific representatives of sarcosinate radicals X⊖ are, in particular, the radicals of the formulae

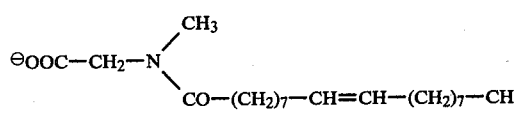 (6)

and, especially,

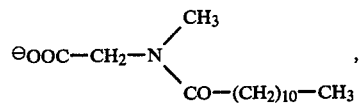 (7)

Examples of sulfate radicals X⊖ (from alkyl-sulfates, and from ether-, ester-, amide- or amino-sulfates) are, in particular, radicals of the formulae

 (8)

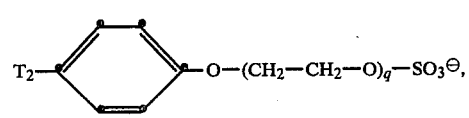 (9)

 (10)

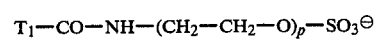 (11)

in which T₁ is as defined and T₂ is alkyl having 6 to 14 carbon atoms, p is an integer from 1 to 50, q is an integer from 6 to 12 and r is an integer from 2 to 6.

T₂ is preferably n-hexyl, n-heptyl, i-octyl, n-octyl, n-nonyl, or n-decyl, or lauryl or myristyl.

Specific representatives of sulfate radicals are, in particular, the radicals of the formulae

⊖O₃S—O—(CH₂)₂₋₄—NH—CO—(CH₂)₁₁—CH₃, (12)

⊖O₃S—(O—CH₂—CH₂)₈₋₁₀—NH—CO—(CH₂)₁₁—CH₃, (13)

 (14)

in particular,

⊖O₃S—(O—CH₂—CH₂)₂—O—(CH₂)₁₁—CH₃ and (15)

⊖O₃S—O—(CH₂)₁₁—CH₃. (16)

Sulfonate radicals X⊖ are radicals of the formulae

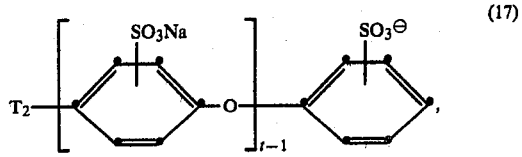 (17)

 (18)

T₂—COO—CH₂—CH₂—SO₃⊖, (19)

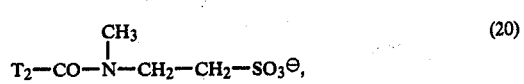 (20)

 (21)

T₁—CH=CH—SO₃⊖ and (22)

 (23)

in which T₁, T₂ and r are as defined, T₁' is the radical as defined for T₁, T₁ and T₁' being identical or different, and t is 1 or 2.

Specific representatives of such sulfonate radicals X⊖ are, in particular, the radicals of the formulae

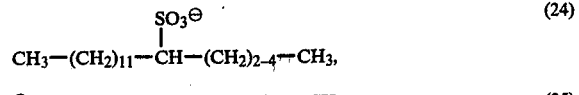 (24)

⊖O₃S—(CH₂)₂—OOC—(CH₂)₁₀—CH₃, (25)

 (26)

and, in particular,

 (27)

and

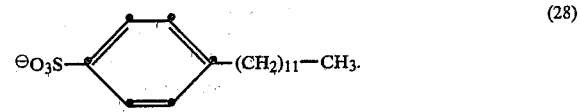 (28)

A sulfosuccinic acid derivative radical X⊖ is, for example, a radical of the formula

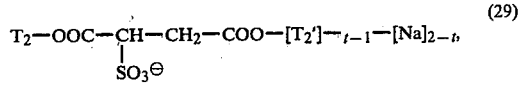 (29)

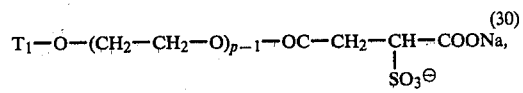 (30)

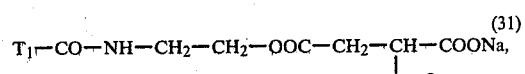 (31)

-continued $$T_1-OOC-CH_2-\underset{\underset{SO_3^{\ominus}}{|}}{CH}-COONa, \quad (32)$$

$$T_2-NH-CO-CH_2-\underset{\underset{SO_3^{\ominus}}{|}}{CH}-COONa, \quad (33)$$

$$\underset{\underset{NaOOC-CH_2}{|}}{NaOOC-CH}-N-CO-CH_2-\underset{\underset{SO_3^{\ominus}}{|}}{CH}-COONa \text{ or} \quad (34)$$
$$\qquad\qquad\qquad T_2$$

$$T_2-N\overset{CO-CH_2}{\underset{CO-CH-SO_3^{\ominus}}{\diagdown}}, \quad (35)$$

in which $T_1$, $T_2$, p and t are as defined and $T_2'$ is the radical as defined for $T_2$, $T_2$ and $T_2'$ being identical or different.

Specific representatives of such radicals $X^{\ominus}$ are the sulfosuccinic acid derivative radicals of the formulae $$^{\ominus}O_3S-CH\overset{CH_2-COO-(CH_2)_7-CH_3}{\underset{COO-(CH_2)_7-CH_3}{\diagdown}}, \quad (36)$$

$$\overset{\ominus O_3S}{\underset{NaOOC}{\diagdown}}CH-CH_2-COO-(CH_2)_7-CH_3, \quad (37)$$

$$\overset{\ominus O_3S}{\underset{NaOOC}{\diagdown}}CH-CH_2-COO-(CH_2)_2-NH-CO-(CH_2)_{10}-CH_3, \quad (38)$$

$$\overset{\ominus O_3S}{\underset{NaOOC}{\diagdown}}CH-CH_2-OOC-(CH_2)_{11}-CH_3, \quad (39)$$

$$\overset{\ominus O_3S}{\underset{NaOOC}{\diagdown}}CH-CH_2-CO-NH-(CH_2)_{11}-CH_3, \quad (40)$$

$$\overset{\ominus O_3S}{\underset{NaOOC}{\diagdown}}CH-CH_2-CO-N\overset{(CH_2)_{10}-CH_3}{\underset{\underset{CH_2-COONa}{CH}}{\diagdown COONa}}, \quad (41)$$

$$\overset{\ominus O_3S-CH-CH_2}{\underset{\underset{(CH_2)_{11}-CH_3}{N}}{O=C\qquad C=O}} \text{ and, in particular,} \quad (42)$$

$$\overset{\ominus O_3S}{\underset{NaOOC}{\diagdown}}CH-CH_2-COO-(CH_2-CH_2-O)_2-(CH_2)_{11}-CH_3. \quad (43)$$

Fluorinated surfactant radicals $X^{\ominus}$ are, in particular, radicals of the formula (44)

in which $T_3$ is perfluorinated alkyl or alkenyl having 6 to 14 carbon atoms.

A possible example of such radicals is the perfluorinated surfactant radical of the formula $$^{\ominus}O_3S-C_6H_4-O-C_{10}F_{19} \quad (45)$$

Phosphate surfactant radicals $X^{\ominus}$ are, in particular, surfactant radicals of the formulae $$T_1-O-\underset{\underset{OM}{|}}{\overset{\overset{O}{\|}}{P}}-O^{\ominus}, \quad (46)$$

$$[T_2-\!\!\bigcirc\!\!-O-]_{2-t}[T_1-O-]_{t-1}(-CH_2-CH_2-O)_{\overline{p}}\overset{\overset{O}{\|}}{\underset{\underset{OM}{|}}{P}}-O^{\ominus} \quad (47)$$

and $$[OH-]_{2-t}[T_2-(O-CH_2-CH_2)_p-]_{t-1}-\overset{\overset{O}{\|}}{\underset{\underset{(CH_2-CH_2-O)_{p'}-T_2'}{|}}{P}}-O^{\ominus} \quad (48)$$

in which M is hydrogen, ammonium, an alkali metal or alkyl having 1 to 3 carbon atoms, $T_1$, $T_2$, $T_2'$, p and t are as defined and p' is the integer as defined for p, p and p' being identical or different.

Examples of such phosphate surfactant radicals are the radicals of the formulae $$^{\ominus}O-\overset{\overset{O}{\|}}{\underset{\underset{ONa}{|}}{P}}-O-(CH_2)_{10}-CH_3, \quad (49)$$

$$^{\ominus}O-\overset{\overset{O}{\|}}{\underset{\underset{OCH_3}{|}}{P}}-(O-CH_2-CH_2)_{12}-O-\!\!\bigcirc\!\!-(CH_2)_8-CH_3, \quad (50)$$

$$^{\ominus}O-\overset{\overset{O}{\|}}{\underset{\underset{OH}{|}}{P}}-(O-CH_2-CH_2)_4-(CH_2)_7-CH=CH-(CH_2)_7-CH_3, \quad (51)$$

$$^{\ominus}O-\overset{\overset{O}{\|}}{\underset{\underset{OH}{|}}{P}}-(O-CH_2-CH_2)_4-(CH_2)_{10}-CH_3 \text{ and} \quad (52)$$

$$^{\ominus}O-\overset{\overset{O}{\|}}{\underset{\underset{(O-CH_2-CH_2)_4-(CH_2)_{10}-CH_3}{|}}{P}}\!\!\!\overset{O-CH_2CH_2)_4-(CH_2)_{10}-CH_3}{\diagup} \quad (53)$$

and mixtures thereof, for example industrial mixtures of phosphate surfactant radicals of the formulae (52) and (53).

Zwitterionic anionic surfactant radicals $X^\ominus$ in formula (1) are surfactant radicals which as a rule have one positive and two negative charges, i.e. ampholytic surfactant radicals which always have an excess of negative charges. Radicals of such zwitterionic anionic surfactants are, in particular, radicals of surface-active N-alkyl-α-iminodipropionates, and especially imidazolinium-dicarboxylic acid derivatives which are alkyl-substituted in the 2-position.

Radicals of alkyl-substituted iminodipropionates are preferably those of the formula

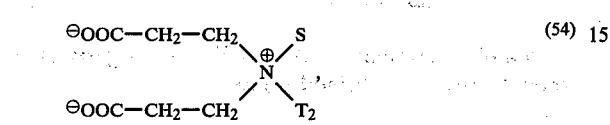
(54)

in which $T_2$ is as defined.

A specific example is the radical of the formula

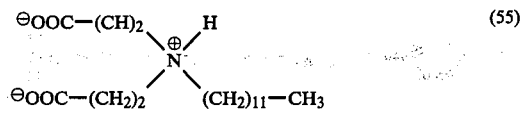
(55)

The preferred imidazolinium radicals of the type mentioned are, in particular, radicals of the formula

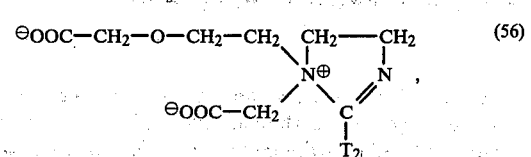
(56)

in which $T_2$ is as defined. Specific examples are the radicals of the formulae

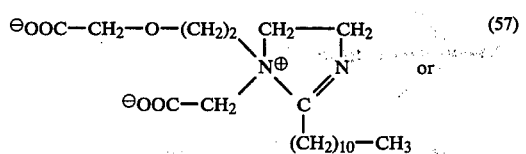
(57)

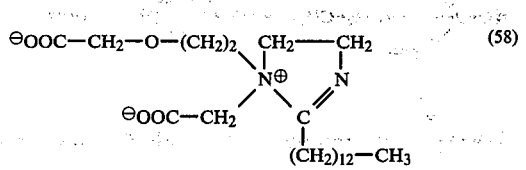
(58)

and industrial mixtures thereof.

Radicals $X^{63}$ in formula (1) which are of particular interest are radicals of surface-active sarcosinates, sulfates, sulfonates, sulfosuccinic acid derivatives and imidazolinium-dicarboxylic acid derivatives, and especially the surfactant radicals of the formulae (7), (15), (16), (18), (27), (28), (43), (57) and (58).

The copolymeric, quaternary ammonium salts according to the invention can be prepared by methods known per se, for example water-in-oil emulsion polymerisation or solution polymerisation. In one preparation process, the comonomers of the formulae $$\begin{array}{c} A_1 \\ | \\ CH_2=C \qquad R_1 \\ | \qquad\qquad | \\ C-D_1-E_1-{}^\oplus N-Q\ Y^\ominus \\ | \\ R_2 \end{array} \qquad (59)$$

$$\begin{array}{c} A_2 \\ | \\ CH_2=C \\ | \\ CO-NH_2 \end{array} \qquad (60)$$

and, in some cases $$\begin{array}{c} A_3 \\ | \\ CH_2=C \quad \text{and,} \\ | \\ G_1 \end{array} \qquad (61)$$

in some cases $$\begin{array}{c} A_4 \\ | \\ CH_2=C \\ | \\ G_2 \end{array} \qquad (62)$$

in which $A_1$, $A_2$, $A_3$, $A_4$, $D_1$, $E_1$, $G_1$, $G_2$, $R_1$, $R_2$ and Q are as defined and $Y^\ominus$ is a halide anion or an alkyl-sulfate or alkyl-phosphonate anion having 1 to 4 carbon atoms in the alkyl radical, are copolymerised by water-in-oil emulsion polymerisation in the presence of a water-in-oil emulsifier and optionally an emulsion stabiliser and a polymerisation initiator, and the copolymer is precipitated with a solvent which is preferably miscible with oil and water, for example methanol, acetone or isopropanol, and is then dried, the preparation process comprising reacting the resulting copolymer with at least one anionic surfactant, which may be zwitterionic, of the formula $$X^\ominus Z^\oplus \qquad (63)$$

in which $Z^\oplus$ is an alkali metal cation or an ammonium cation which is unsubstituted or substituted by alkyl or alkanol radicals having 1 to 4 carbon atoms and $X^\ominus$ is as defined, in an aqueous medium at 10° to 60° C. and at a pH value of 5 to 9, the anion $Y^\ominus$ being replaced by the anion $X^\ominus$.

If the solution polymerisation method is used, it is not necessary to employ emulsifiers and emulsion stabilisers. Water is as a rule used as the solvent.

Hydrophobic, organic liquids are required for the oil phase in the water-in-oil emulsion polymerisation. Suitable oils for this purpose are, for example, aliphatic or aromatic hydrocarbons, oils of animal or vegetable origin and the corresponding denatured oils (for example hydrogenated oils or polymerised oils). Preferred hydrophobic organic liquids are aliphatic hydrocarbons, such as kerosene, paraffin and isoparaffin, and aromatic hydrocarbons, such as benzene, toluene and xylene. Commercially available industrial mixtures of preferably branched paraffin oils with a boiling range from 160° to 260° C., preferably 180° to 210° C., are of particular interest.

Water-in-oil emulsifiers which are used in the inverse emulsion polymerisation are polyoxyalkylene adducts, preferably polyoxyethylene adducts, of aliphatic alcohols having 8 to 24 carbon atoms, such as lauryl, cetyl, stearyl and oleyl alcohol, of fatty acids of the abovementioned type having 8 to 24 carbon atoms, preferably lauric, palmitic, stearic and oleic acid, of alkylphenols having 3 to 24 carbon atoms in the alkyl radical, for example octyl-, nonyl-, dodecyl- and dinonyl-phenol, and of esters of fatty acids of the type mentioned and polyhydric alcohols, for example glycerol, pentaerythritol, sorbitol and sorbitan. Commercially available mixtures, i.e. polyoxyalkylene adducts of industrial alcohol mixtures, fatty acid mixtures, alkylphenol mixtures and ester mixtures, are also particularly suitable for use as water-in-oil emulsifiers. However, esters of fatty acids of the type mentioned or of fatty acid mixtures and polyhydric alcohols of the type mentioned are particularly preferred, sorbitan monooleate being of special interest.

In particular cases, it has proved advantageous to use an emulsion stabiliser in the oil phase. Stabilisers which are suitable for this purpose are, in particular, rubbers which are soluble in the oil phase, that is to say both rubbers of natural origin, for example crystal gum, and, preferably, those of synthetic origin, for example polybutadiene, styrene/butadiene copolymers and, in particular, polyisoprene. Polyisoprene is of special interest.

As a rule, the oil phase contains about 2 to 15 percent by weight of emulsifier and 0 to about 1, preferably 0.4 to 0.8, percent by weight of stabiliser.

After the oil phase has been mixed with the aqueous phase, which contains the comonomers of the formulae (59), (60) and optionally (61) and (62), the copolymerisation is as a rule started by adding a polymerisation initiator. The initiators employed can be the usual polymerisation catalysts, preferably in the form of their aqueous solutions, for example azo compounds, such as azo-bis(isobutyronitrile) or azo-bis(dimethylvaleronitrile), oxidising agents, preferably peroxides, such as hydrogen peroxide or benzoyl peroxide, or, preferably, persulfates, such as ammonium persulfate, and also chlorates or chromates, reducing agents, such as sulfites, bisulfites, oxalic acid and ascorbic acid, and combinations of the abovementioned oxidising and reducing agents, as so-called redox catalysts. In the present case, sodium sulfite is a particularly suitable initiator.

The copolymerisation as a rule takes place at 30° to 90° C., preferably 40° to 70° C., and can also proceed as an exothermic reaction, so that it may be necessary to maintain the polymerisation temperature by cooling.

For usual working up of the product, the resulting copolymer is as a rule precipitated by a solvent which is preferably miscible with oil and water, for example methanol, isopropanol or acetone, the precipitation generally being carried out by adding the water-in-oil emulsion to the solvent, preferably at room temperature (15° to 25° C.), after which the polymer which has precipitated is filtered off and dried, preferably at temperatures of at most 60° C. and in particular at temperatures from about 30° to 50° C., reduced pressure being advantageous.

The resulting water-in-oil copolymers known per se are now converted by methods known per se into the novel copolymeric quaternary ammonium salts according to the invention which contain structural elements of the formula (1). For this purpose, the resulting water-in-oil copolymers are reacted with the surfactant of the formula (63) as described above, the reaction preferably being carried out at temperatures from 15° to 40° C. for 30 to 100, in particular 60 to 90, minutes. An excess of at least one anionic surfactant, which may be zwitterionic, of the formula (63), based on the comonomeric quaternary ammonium salt of the formula (59) used in the preparation of the copolymer, is as a rule employed. This excess is about 4 to 500, preferably 5 to 120 and in particular 7 to 70, mols of surfactant per mol of the monomeric ammonium salt used.

When used in the cosmetics industry, the novel, copolymeric quaternary ammonium salts according to the invention are preferably employed as hair cosmetics.

The cosmetics, preferably hair cosmetics, according to the invention as a rule contain an excess of at least one of the anionic surfactants, which may be zwitterionic, of the formula (63) used in the preparation of the ammonium salts, in addition to the novel copolymeric quaternary ammonium salts.

In their preferred embodiment, the cosmetics are in the form of aqueous hair cosmetics which contain 0.05 to 1.5, preferably 0.2 to 1.0, parts by weight, calculated as effective substance, of at least one polymeric ammonium salt having structural elements of the formula (1), (2), and optionally (3) and/or (4), 5 to 20, preferably 8 to 15 and in particular 9 to 12, parts by weight, calculated as effective substance, of at least one anionic surfactant, which may be zwitterionic, of the formula (63) and optionally cosmetic assistants, and are diluted to a total of 100 parts by weight with demineralised water.

The cosmetic assistants which may be present are commercially available agents such as are used in hair cosmetics. These agents are, for example, surfactants other than the surfactants of the formula (63), such as polyglycerol esters of fatty acids, in particular polyglycerol oleates, or soaps, in particular the stearates of sodium, aluminum, magnesium, zinc or calcium, foam stabilisers, for example fatty acid polyalkanolamides, thickeners of natural or synthetic origin, such as hydroxypropylmethylcellulose and polyacrylic acid, opalising agents, such as fatty acid monoalkanolamides or, preferably, glycerol monostearate, and also, inter alia, preservatives, perfumes and pearlescent agents.

If required, the hair cosmetics are adjusted to a pH value of 5 to 8, preferably 7.0 to 7.5, or, even more preferably, 7.0 to 7.2 which can advantageously be achieved by addition of, inter alia, an aqueous solution of, for example, sodium hydroxide or citric acid.

When the aqueous hair cosmetic described above is used for hair treatment, preferably on human hair, it is applied to hair which has been wetted with tapwater, as a rule at room temperature or slightly elevated temperature, for example 20° to 40° C., and the hair is then shampooed and conditioned. The hair treated in this way can also be in the form of wigs or toupees.

The essential advantage of the present invention is that application of the hair cosmetics which contain copolymeric quaternary ammonium salts having structural elements of the formula (1) comprising the corresponding water-in-oil copolymers with high molecular weight components and surfactants of the formula (63) gives the treated hair excellent combing properties when dry and, in particular, when wet. In particular, the ease of wet combing of hair treated with the hair cosmetics according to the invention is clearly superior to that of hair treated with conventional cosmetics. The latter indeed also contain mixtures and/or reaction products of surfactants and copolymers, but the copolymers have a different composition and, in particular, they lack the high molecular weight components.

In the preparation instructions and examples which follow, parts and percentages are by weight.

Preparation instructions of water-in-oil emulsion copolymers

Instructions A:

The following three solutions are prepared in an oxygen-free, inert nitrogen atmosphere:

Solution I (oil phase)

500 parts of a branched paraffin oil (industrial mixture, molecular weight: 171, boiling range: 188°–206° C.) are introduced into a double-walled reaction vessel. 140 parts of a 2.5% solution of a synthetic polyisoprene rubber (emulsion stabiliser) in paraffin oil of the type described and then 78 parts of sorbitan monooleate (water-in-oil emulsifier) are added to the paraffin oil at 20° C., with stirring.

A clear, yellowish solution is obtained.

Solution II (aqueous phase)

568.6 parts (8 mols) of acrylamide are dissolved in 700 parts of demineralised, oxygen-free water at 20° C. 220 parts of sodium chloride are introduced into this solution, with stirring, and 1,133.2 parts of a 50% aqueous solution of methacryloyloxyethyl-trimethylammonium methyl-sulfate (2 mols) are then added.

A clear, colourless solution is obtained.

Solution III (initiator solution)

0.66 part of sodium sulfite are dissolved in 40 parts of demineralised, oxygen-free water.

Copolymerisation reaction

Solution II is added to solution I at 20° C. in an inert nitrogen atmosphere in the cource of 10 minutes, with intensive stirring (3,000 rpm). A homogeneous, white emulsion is obtained, and stirring is continued at 20° C. until the viscosity of a sample of the emulsion is 14,000 mPa.s (Brockfield Viscosimeter LV, spindle 3, 6 rpm, 25° C.), which generally takes 10 minutes. Thereafter, the reaction mixture is heated to 40° C. in the course of 30 minutes, with stirring at 300 rpm. Solution III is now added to the reaction mixture by means of a metering pump in the course of 150 minutes, the temperature being kept at 40° to 41° C. by cooling. When the initiator solution has been added, stirring of the reaction mixture is continued at 40° C. and 300 rpm until the viscosity of a sample of the emulsion has fallen to 7,600 mPa.s (Brookfield Viscosimeter LV. spindle 1, 60 rpm, 25° C.), which generally takes one hour.

Working up

The resulting emulsion of the copolymer is poured into 24,000 parts of acetone at 20° C., with stirring, and the copolymer is precipitated. The precipitate is filtered off and dried at 40° C. under reduced pressure for 2 days. 1,100 parts of a copolymer which contains, in any order, 80 mol % of structural elements of the formula

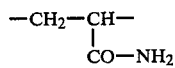 (64)

and 20 mol % of structural elements of the formula

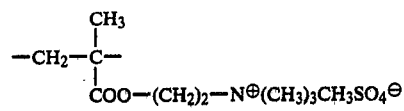 (65)

are obtained. 37% of the copolymer has a molecular weight between $10^7$ and $10^9$.

Instructions B

The procedure described in instructions A is repeated, using 1,108 parts of a 40% aqueous solution of methacryloyloxypropyl-trimethylammonium chloride (2 mols) in the aqueous phase (solution II).

1,000 parts of a copolymer which contains, in any order, 80 mol % of structural elements of the formula (64) given in instructions A and 20 mol % of structural elements of the formula

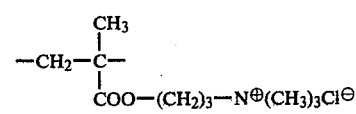 (66)

are obtained. 27% of the copolymer has a molecular weight between $10^7$ and $10^9$.

Instructions C

The procedure described in instructions A is repeated, using 1,622 parts of a 40% aqueous solution of methacryloyl-amidopropyl-diethyl-methylammonium methylsulfate (2 mols) in the aqueous phase (solution II).

648.8 parts of a copolymer which contains, in any order, 80 mol % of structural elements of the formula (64) given in instructions A and 20 mol % of structural elements of the formula

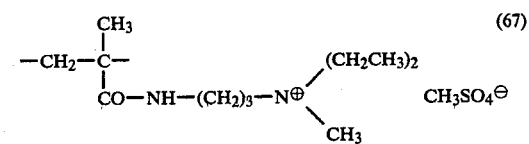 (67)

are obtained. 7% of the copolymer has a molecular weight between $10^7$ and $10^9$.

Instructions D

The procedure described in instructions A is repeated, using 1,471.5 parts of a 40% aqueous solution of methacryloylxypropyl-dimethyl-n-propylammonium bromide (2 mols) in the aqueous phase (solution II).

1,000 parts of a copolymer which contains, in any order, 80 mol % of structural elements of the formula (64) given in instructions A and 20 mol % of structural elements of the formula

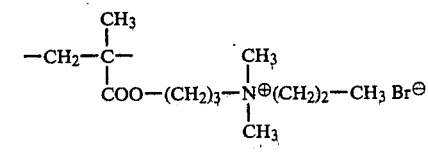 (68)

are obtained. 22% of the copolymer has a molecular weight between $10^7$ and $10^9$.

Instructions E

The procedure described in instructions A is repeated, employing the following solutions I, II and III, and using 40,000 parts of acetone in the working up operation.

Solution I 825 parts of the paraffin oil described in instructions A, 269 parts of the 2.5% rubber solution described in instructions A and 255 parts of sorbitan monooleate.

Solution II

An aqueous solution of 681.6 parts (9.6 mols) of acrylamide, 34.6 parts (0.48 mol) of acrylic acid, 50.3 parts (0.32 mol) of ethyl dimethylamino-methacrylate and 220 parts of sodium chloride in 700 parts of water, and an aqueous solution of 1,586.5 parts (5.6 mols) of methacryloyloxyethyl-trimethylammonium methyl-sulfate in 3,100 parts of water.

Solution III 1.07 parts of sodium sulfite in 66.8 parts of water.

2,100 parts of a copolymer which contains, in any order, 60 mol % of structural elements of the formula (64) given in instructions A, 35 mol % of structural elements of the formula (65) given in instructions A, 3 mol % of structural elements of the formula

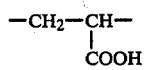  (69)

and 2 mol % of structural elements of the formula

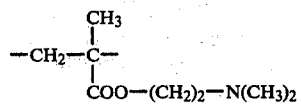  (70)

are obtained. 12% of the copolymer has a molecular weight between $10^7$ and $10^9$.

Instructions F

The procedure described in instructions A is repeated, employing the following solutions, I, II and III and using 50,000 parts of acetone in the working up operation.

Solution I*

1,628 parts of the paraffin oil described in instructions A and 191 parts of sorbitan monooleate. (* in contrast to instructions A, contains no rubber solution).

Solution II

A solution of 1,516.6 parts (21.36 mols) of acrylamide, 679.9 parts (2.40 mols) of methacryloyloxyethyl-trimethylammonium methyl-sulfate, 37.7 parts (0.24 mol) of ethyl dimethylamino-methacrylate and 600 parts of sodium chloride in 2,550 parts of water. ( in contrast to instructions A, these components are not added separately).

Solution III 1.6 parts of sodium sulfite and 720 parts of water 1,890 parts of a copolymer which contains, in any order, 90 mol % of structural elements of the formula (64) given in instructions A, 9 mol % of structural elements of the formula (65) given in instructions A and 1 mol % of structural elements of the formula (70% given in instructions E, are obtained. 23% of the copolymer has a molecular weight between $10^7$ and $10^9$.

Preparation instructions for a solution copolymer

Instructions G:

The following two solutions are prepared in an oxygen-free inert nitrogen atmosphere:

Solution 1 (monomer solution)

71.1 parts (1 mol) of acrylamide and 141.7 parts of a 50% aqueous solution of methacryloyloxyethyl-trimethylammonium methyl-sulfate (0.25 mol) are dissolved in 228 parts of demineralised, oxygen-free water in a double-walled vessel at 20° C.

A clear colourless solution is obtained.

Solution II (initiator solution)

0.2 part of ammonium peroxodisulfate are dissolved in 150 parts of demineralised, oxygen-free water.

Copolymerisation reaction

Half of solution II is added to solution I at 35° C. in an inert nitrogen atmosphere in the course of 1 minute, with stirring. After 6 hours, the reaction solution is warmed to 50° C. and the second half of solution II is added. The mixture is stirred for 2 to 3 hours until a highly viscous solution has formed. The reaction mixture is left to stand, without stirring. After 24 hours, the resulting colourless gel is allowed to cool.

Working up

The gel is comminuted, and dissolved in 1,350 parts of demineralised water. The highly viscous solution is then extruded as a thin strand at 20° C. into 18,000 parts of acetone, and the copolymer is precipitated. It is then filtered off and kneaded again in 1,800 parts of acetone until it becomes hard and brittle. It is again filtered off, and is dried under reduced pressure at 40° C. for 2 days. 110 parts of a copolymer which contains, in any order, 80 mol % of structural elements of the formula

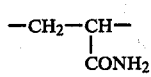

and 20 mol % of structural elements of the formula

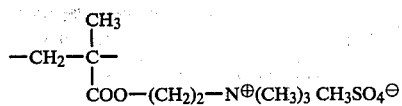

are obtained. 12% of the copolymer has a molecular weight between $10^7$ and $10^9$.

EXAMPLE 1

100 parts of an aqueous solution containing 1.71 parts of the copolymer according to instructions A (3 m-equivalents, based on the quaternary content of the copolymer) are added to a solution of 24.9 parts of the surfactant of the formula

  (71)

(70 mmols or 23.3 mols per mol of the comonomeric, quaternary ammonium salt used in instructions A) in 150 parts of water at 35° C. in the course of 80 minutes, reaction of the quaternary structural elements of the copolymer with the surfactant employed simultaneously taking place, with ion exchange. 250 parts of an

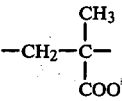

equeous, slightly opalescent, viscous solution containing 9.5% of surfactant of the abovementioned formula (71) and 0.9% of a copolymer which comprises, in any order, 80 mol % of structural elements of the formula (64) given in instructions A and 20 mol % of structural elements of the formula

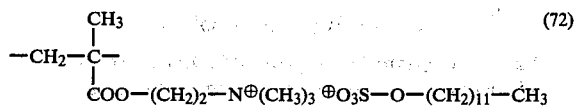

are obtained.

EXAMPLE 2

The procedure described in Example 1 is repeated, using 7.7 parts of the surfactant of the formula $$CH_3(CH_2)_{11}-O-(CH_2-CH_2-O)_2-SO_2Na \quad (73)$$

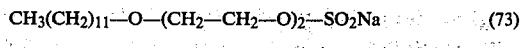

(20 mmols or 6.67 mols per mol of the comonomeric, quaternary ammonium salts used in instructions A).

250 parts of an aqueous, slightly opalescent solution containing 2.6% of surfactant of the abovementioned formula (73) and 1.0% of a copolymer which comprises, in any order, 80 mol % of structural elements of the formula (64) given in instructions A and 20 mol % of structural elements of the formula

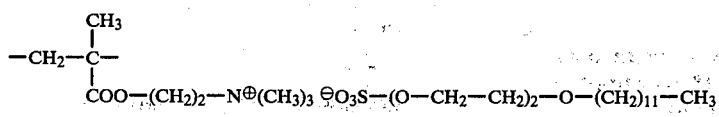

are obtained.

EXAMPLE 3

The procedure described in Example 1 is repeated, using 29.3 parts of the surfactant of the formula

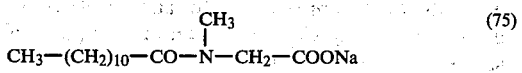

(100 mmols or 33.3 mols per mol of the comonomeric, quaternary ammonium salt used in instructions A). 250 parts of an aqueous, slightly opalescent viscous solution containing 11.3% of the surfactant of the abovementioned formula (75) and 0.9% of a copolymer which comprises, in any order, 80 mol % of structural elements of the formula (64) given in instructions A and 20 mol % of structural elements of the formula

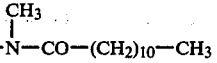

are obtained.

EXAMPLE 4

The procedure described in Example 1 is repeated, using 25.7 parts of the surfactant of the formula

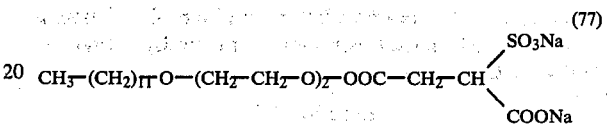

(50 mmols or 16.7 mols per mol of the comonomeric, quaternary ammonium salt used in instructions A).

250 parts of an aqueous, slightly opalescent solution containing 9.7% of surfactant of the abovementioned formula (77) and 1.1% of a copolymer which comprises, in any order, 80 mol % of structural elements of the formula (64) given in instructions A and 20 mol % of structural elements of the formula

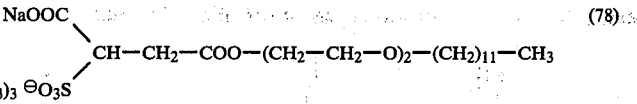

EXAMPLE 5

The procedure described in Example 1 is repeated, using 25.2 parts of the surfactant of the formula

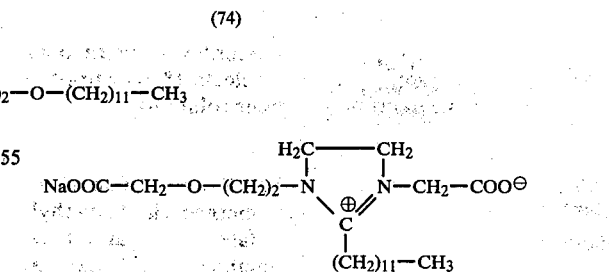

(60 mmols or 20 mols per mol of the comonomeric, quaternary ammonium salt used in instructions A).

250 parts of an aqueous, slightly opalescent solution containing 9.6% of surfactant of the abovementioned formula (79) and 1.1% of a copolymer which comprises, in any order, 80 mol % of structural elements of the formula (64) given in instructions A and 20 mol % of structural elements of the formula

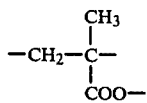
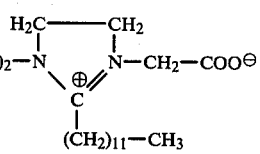

(80)

EXAMPLE 6

The procedure described in Example 1 is repeated, using 24.4 parts of the surfactant of the formula

(81)

(70 mmols or 22.3 mols per mol of the comonomeric, quaternary ammonium salt used in instructions A).

250 parts of an aqueous, slightly opalescent solution containing 9.3% of surfactant of the abovementioned formula (81) and 0.85% of a copolymer which comprises, in any order, 80 mol % of structural elements of the formula (64) given in instructions A and 20 mol % of structural elements of the formula

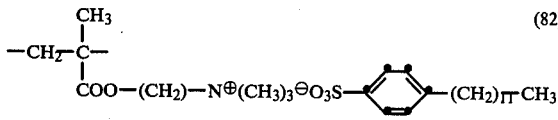

(82)

are obtained.

EXAMPLE 7

100 parts of an aqueous solution containing 2.02 parts of the copolymer according to instructions B (4 mequivalents, based on the quaternary content of the copolymer) are added to a solution of 105 parts of the surfactant of the formula (79) given in Example 5 (250 mmols or 62.5 mols per mol of the comonomeric, quaternary ammonium salt used in instructions B) in 900 parts of water at 25° C. in the course of 1 hour, the reaction of the quaternary structural elements of the copolymer with the surfactant employed simultaneously taking place, with ion exchange. 1,000 parts of an aqueous, slightly opalescent, viscous solution containing 10.4% of surfactant of the abovementioned formula (79) and 0.31% of a copolymer which comprises, in any order, 80 mol % of structural elements of the formula (64) given in instructions A and 20 mol % of structural elements of the formula (80) given in Example 5 are obtained.

EXAMPLE 8

The procedure described in Example 7 is repeated, using 104 parts of the surfactant of the formula (71) given in Example 1 (250 mmols or 62.5 mols per mol of the comonomeric, quaternary ammonium salt used in instructions B).

1,000 parts of an aqueous, slightly opalescent solution containing 1.03% of the surfactant of the abovementioned formula (71) and 0.3% of a copolymer which comprises, in any order, 80 mol % of structural elements of the formula (64) given in instructions A and 20 mol % of structural elements of the formula (72) given in Example 1, are obtained.

EXAMPLE 9

10 parts of an aqueous solution containing 0.168 part of the copolymer according to instructions E (0.4 m-equivalent, based on the quaternary content of the copolymer) are added to a solution of 10.5 parts of the surfactant of the formula (71) given in Example 1 (5.71 mmols or 14.3 mols per mol of the comonomeric ammonium salt used in instructions E) in 90 parts of water at 35° C. in the course of 90 minutes, the reaction of the quaternary structural elements of the copolymer with the surfactant employed simultaneously taking place, with ion exchange. 100 parts of an aqueous, slightly opalescent, viscous solution containing 9.8% of surfactant of the abovementioned formula (71) and 0.38% of a copolymer which comprises, in any order, 60 mol % of structural elements of the formula (64) given in instructions A, 3 mol % of structural elements of the formula (69) given in instructions E, 2 mol % of structural elements of the formula (70) given in instructions E and 35 mol % of structural elements of the formula (72) given in Example 1, are obtained.

EXAMPLE 10

35 parts of an aqueous solution containing 0.65 part of the copolymer according to instructions E (0.7 mequivalent, based on the quaternary content of the copolymer) are added to a solution of 13.7 parts of the surfactant of the formula

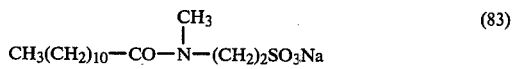

(83)

(40 mmols or 57.1 mols per mol of the comonomeric, quaternary ammonium salt used in instructions E) in 65 parts of water at 30° C. in the course of 75 minutes, reaction of the quaternary structural elements of the copolymer with the surfactant employed simultaneously taking place, with ion exchange.

100 parts of an aqueous, slightly opalescent, viscous solution containing 13.5% of surfactant of the abovementioned formula (83) and 0.75% of a copolymer which comprises, in any order, 90 mol % of structural elements of the formula (64) given in instructions A, 1 mol % of structural elements of the formula (69) in instructions E and 9 mol % of structural elements of the formula

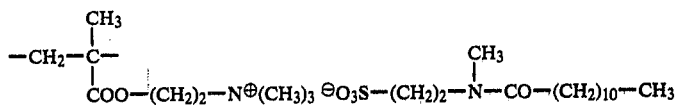

(84)

are obtained.

EXAMPLE 11

50 parts of an aqueous solution containing 0.58 part of the copolymer according to instructions D (1 mequivalent, based on the quaternary content of the copolymer) are added to a solution of 11.6 parts of the surfactant of the formula (73) given in Example 2 (30 mmols, i.e. 30 mols per mol of the comonomeric quaternary ammonium salt used in instructions D) in 50 parts of water at 45° C. in the course of 50 minutes, reaction of the quaternary structural elements of the copolymer with the surfactant employed simultaneously taking place, with ion exchange.

100 parts of an aqueous, slightly opalescent viscous solution containing 11.2% of surfactant of the abovementioned formula (73) and 0.87% of a copolymer which comprises, in any order, 80 mol % of structural elements of the formula (64) given in instructions A and 20 mol % of structural elements of the formula

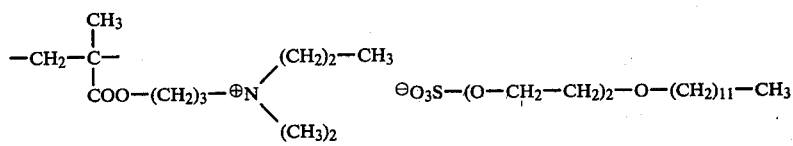

(85)

are obtained.

EXAMPLE 12

The aqueous solution according to Example 1 is adjusted to a pH value of 7.1 by addition of 10% aqueous citric acid solution, and is used to treat a wig, which has been wetted with tapwater, of unbleached, undyed, brown human hair of European origin by three applications in a so-called half-head test at 30° C., after which the hair of the wig is shampooed and conditioned at this temperature. In the half-head test, one half of the wig is shampooed and conditioned with the solution described above, whilst the other half of the wig is shampooed under the same conditions but using a solution containing only surfactant and no copolymer according to the invention. In this so-called blank formulation, the copolymer is replaced by the appropriate amount of surfactant, so that, for example in comparison with Example 1, the blank formulation contains 10.4% of surfactant of the formula (71) given in Example 1, the pH value of the blank formulation likewise being adjusted to 7.1 with aqueous 10% citric acid solution. After each application, the ease of wet and dry combing of the half of the wig treated according to the invention is evaluated in comparison with the half of the wig treated with the blank formulation, the following scale of ratings being used:

+3 much better than the blank formulation
+2 better than the blank formulation
+1 somewhat better than the blank formulation
0 no different to the blank formulation
−1 somewhat poorer than the blank formulation
−2 poorer than the blank formulation
−3 much poorer than the blank formulation.

The combing ratings achieved using the solution according to Example 1 are summarised in Table I.

TABLE I

|  | after the 1st application | after the 2nd application | after the 3rd application |
|---|---|---|---|
| Wet combing rating | +2 | +3 | +3 |
| Dry combing rating | +2 | +(2-3) | +3 |

Similar results are achieved with the aqueous solution according to Example 3 and the corresponding blank formulation.

EXAMPLE 13

The procedure described in Example 12 is repeated, using the aqueous solution according to Example 4 and the corresponding blank formulation.

The combing ratings achieved are summarised in Table II.

TABLE II

|  | after the 1st application | after the 2nd application | after the 3rd application |
|---|---|---|---|
| Wet combing rating | +(1-2) | +(1-2) | +(1-2) |
| Dry combing rating | +1 | +(1-2) | +(1-2) |

EXAMPLE 14

The procedure described in Example 12 is repeated, using the aqueous solution according to Example 5 and the corresponding blank formulation.

The combing ratings achieved are summarised in Table III.

TABLE III

|  | after the 1st application | after the 2nd application | after the 3rd application |
|---|---|---|---|
| Wet combing rating | +(1-2) | +2 | +2 |
| Dry combing rating | +(0-1) | +(0-1) | +1 |

Similar results are achieved with the aqueous solutions according to Examples 6 and 7 and the corresponding blank formulations.

EXAMPLE 15

The procedure described in Example 12 is repeated, using the aqueous solution according to Example 8 and the corresponding blank formulation.

The combing ratings achieved are summarised in Table IV.

TABLE IV

|  | after the 1st application | after the 2nd application | after the 3rd application |
|---|---|---|---|
| Wet combing rating | +(0-1) | +1 | +1 |
| Dry combing rating | +1 | +(0-1) | +1 |

EXAMPLE 16

The procedure described in Example 12 is repeated, using the aqueous solution according to Example 2 and the corresponding blank formulation.

The combing ratings achieved are summarised in Table V.

TABLE V

|  | after the 1st application | after the 2nd application | after the 3rd application |
|---|---|---|---|
| Wet combing rating | +1 | +2 | +(1-2) |
| Dry combing rating | +1 | +2 | +2 |

Similar results are achieved with the aqueous solution according to Example 8 and the corresponding blank formulation.

EXAMPLE 17

The procedure described in Example 12 is repeated, using the aqueous solution according to Example 9 and the corresponding blank formulation.

The wet combing ratings achieved are +1 after the 1st application and in each case +(1-2) after the 2nd and 3rd application.

EXAMPLE 18

The procedure described in Example 12 is repeated, using the aqueous solution according to Example 10 and the corresponding blank formulation.

The combing ratings achieved are summarised in Table VI.

TABLE VI

|  | after the 1st application | after the 2nd application | after the 3rd application |
|---|---|---|---|
| Wet combing rating | +2 | +2 | +2 |
| Dry combing rating | +1 | +1 | +1 |

Similar results are achieved with the aqueous solution according to Example 11 and the corresponding blank formulation.

EXAMPLE 19

100 parts of a copolymer comprising 74 mol % of structural elements of the formula (64) and 26 mol % of elements of the formula (65) are pulverised and the powder is stirred with a mixture of 400 parts of methanol and 100 parts of water at room temperature for 30 minutes. A further 500 parts of methanol are added and the mixture is stirred for another 5 minutes and then left to stand for one hour. The gelatinous sludge is then filtered in a pressure filter under a pressure of 3 bars. The gelatinuous mass is then suspended in 100 parts of methanol and the suspension is filtered again under pressure. After three treatments with methanol, the product is dried in vacuo at 40° C. for one day.

According to the values obtained by means of gel permeation chromatography, the molecular weight distribution in the starting polymer (A) and in the polymer (B) treated in accordance with the above instructions is as follows:

| Polymer | $M \geq 10^7$ | $M = 10^5 - 10^7$ | $M < 10^5$ |
|---|---|---|---|
| A | 20% | 29% | 51% |
| B | 39% | 48% | 13% |

Formulations of the two polymers A and B are prepared by the procedure described in Example 1 by adding in each case a solution of 1.4 parts of one of the two polymers in 80 parts of water to a solution of 20 parts of the compound of the formula $$CH_3(CH_2)_{11}OSO_3H.N(CH_2CH_2OH)_3$$

in 120 parts of water.

When these formulations are tested on wigs in the half-head test as described in Example 12, they both give better ease of wet combing compared with the blank formulation.

This effect, however, is more pronounced in the case of the formulation ontaining the purified polymer B.

|  | Wet combing rating | | |
|---|---|---|---|
|  | after the 1st application | after the 2nd application | after the 3rd application |
| Formulation containing Polymer A | +1-2 | +2 | +2 |
| Formulation containing Polymer B | +2 | +3 | +3 |

What is claimed is:

1. A copolymeric, quaternary ammonium salt which is soluble or forms a microemulsion in an aqueous surfactant system, which has a molecular weight distribution of $10^4$ to $10^9$, the molecular weight of at least 5 percent by weight of the copolymer being $10^7$ to $10^9$, and comprises, in any order, recurring structural elements of the formulae

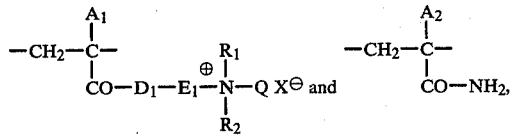

in which $A_1$ and $A_2$ are each hydrogen or methyl, $D_1$ is oxygen or —NH—, $E_1$ is alkylene having 1 to 4 carbon atoms which is unsubstituted or substituted by hydroxyl, $R_1$ and $R_2$ are each methyl or ethyl, Q is alkyl or hydroxy-alkyl having 1 to 4 carbon atoms or benzyl and $X^\ominus$ is the redical of at least one anionic sulfosuccinate surfactant.

2. An ammonium salt according to claim 1, which is obtained by water-in-oil emulsion polymerization or a solution polymerization of a quaternary ammonium salt of the acrylic acid series and at least one other acrylic comonomer, isolation of the copolymer and reaction thereof with an anionic sulfosuccinate surfactant, ion exchange taking place.

3. An ammonium salt according to claim 1, which contains on average 5 to 80 mol % of structural elements of the formula

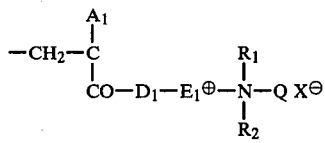

and on average 10 to 95 mol % of structural elements of the formula

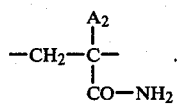

4. An ammonium salt according to claim 1, in which the molecular weight of 5 to 60 percent by weight of the copolymer is $10^7$ to $10^9$.

5. An ammonium salt according to claim 1, in which $X^\ominus$ is a sulfosuccinic acid derivative radical of the formula

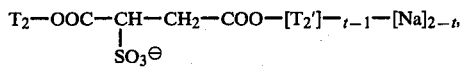

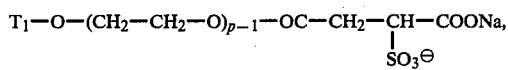

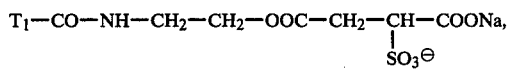

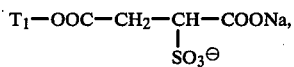

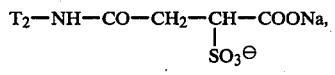

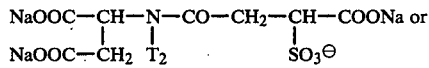

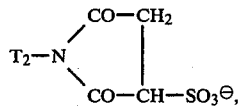

in which $T_1$ is alkyl or alkenyl having 7 to 21 carbon atoms, $T_2$ and $T_2'$ are each alkyl having 6 to 14 carbon atoms, p is an integer from 1 to 50 and t is 1 or 2.

6. A copolymeric, quaternary ammonium salt which is soluble or forms a microemulsion in an aqueous surfactant system, which has a molecular weight distribution of $10^4$ to $10^9$, the molecular weight of at least 5 percent by weight of the copolymer being $10^7$ to $10^9$, and which is obtained by water-in-oil emulsion polymerization, in the presence of a water-in-oil emulsifier and, optionally, an emulsion stabilizer, or by solution polymerization, in each case in the presence of a polymerization initiator, of comonomers of the formulae

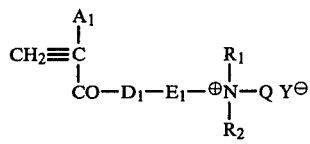

and

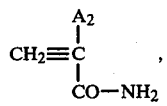

in which $A_1$, $A_2$, $D_1$, $E_1$, Q, $R_1$ and $R_2$ are as defined in claim 1 and $Y^\ominus$ is a halide anion or an alkyl-sulfate or alkyl-phosphonate anion having 1 to 4 carbon atoms in the alkyl radical, subsequent precipitation of the copolymer with a water-soluble solvent, drying of the copolymer and reaction thereof with at least one surfactant of the formula $$X^\ominus Z^\oplus$$

in which $Z^\oplus$ is an alkali metal cation or an ammonium cation which is unsubstituted or substituted by alkyl or alkanol radicals having 1 to 4 carbon atoms and $X^\ominus$ is as defined in claim 1, in an aqueous medium at 10° to 60° C. and at a pH value of 5 to 9, the anion $Y^\ominus$ being replaced by the anion $X^\ominus$.

7. A cosmetic which contains at least one polymeric ammonium salt according to claim 1.

8. A cosmetic which contains at least one of the polymeric salts and an excess of at least one of the anionic sulfosuccinate surfactants, of the formula of claim 6 used in the preparation of the ammonium salt.

9. A cosmetic according to claim 7 which is a hair cosmetic.

10. A hair cosmetic according to claim 9, which contains 0.05 to 1.5 parts by weight, calculated as effective substance, of at least one polymeric ammonium salt, 5 to 20 parts by weight, calculated as effective substance, of at least one anionic sulfosuccinate surfactant, and, optionally, a cosmetic assistant and is diluted with demineralized water to a total of 100 parts by weight.

11. A hair cosmetic according to claim 10, which is adjusted to a pH value of 7.0 to 7.5 with an aqueous solution of sodium hydroxide or citric acid.

12. A method of hair treatment to give ease of wet and dry combing which comprises the step of applying a cosmetic which contains at least one copolymeric, quaternary ammonium salt which is soluble or forms a microemulsion in an aqueous surfactant system, which has a molecular weight distribution of $10^4$ to $10^9$, the molecular weight of at least 5 percent by weight of the copolymer being $10^7$ and $10^9$, and comprises, in any order, recurring structural elements of the formulae

in which $A_1$ and $A_2$ are each hydrogen or methyl, $D_1$ is oxygen or —NH—, $E_1$ is alkylene having 1 to 4 carbon atoms which is unsubstituted or substituted by hydroxyl, $R_1$ and $R_2$ are each methyl or ethyl, Q is alkyl or hydroxy-alkyl having 1 to 4 carbon atoms or benzyl and $X^{\ominus}$ is the radical of at least one anionic sulfosuccinate surfactant.

13. The method of claim 12 wherein the cosmetic contains 0.05 to 1.5 parts by weight, calculated as effective substance, of the polymeric ammonium salt, 5 to 20 parts by weight, calculated as effective substance, of at least one anionic sulfosuccinate surfactant, and is diluted with demineralized water to a total of 100 parts by weight.

14. The method of claim 13 wherein the cosmetic is adjusted to a pH value of 7.0 to 7.5 with an aqueous solution of sodium hydroxide or citric acid.

* * * * *

UNITED STATES PATENT AND TRADEMARK OFFICE
CERTIFICATE OF CORRECTION

PATENT NO. : 4,460,569

DATED : July 17, 1984

INVENTOR(S) : Dieter Strasilla, Hubert Meindl, Laszlo Moldovanyi, and Charles Fearnley It is certified that error appears in the above-identified patent and that said Letters Patent is hereby corrected as shown below:

Claim 6, Column 24, Lines 2-12 should read--

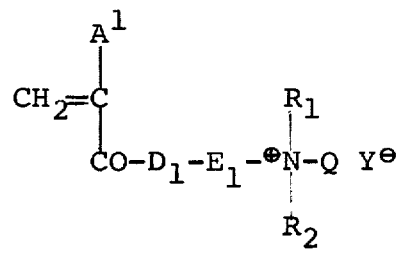

and

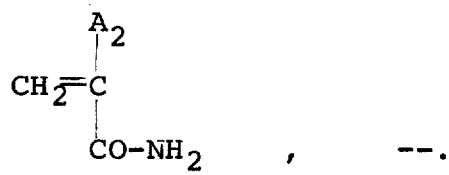

Signed and Sealed this

Twenty-fourth Day of September 1985

[SEAL]

Attest:

Attesting Officer

DONALD J. QUIGG

Commissioner of Patents and Trademarks—Designate